United States Patent [19]

Bartels

[11] 4,190,045
[45] Feb. 26, 1980

[54] NOISE REDUCING EXHALATION VALVE AND DIAPHRAGM

[75] Inventor: Harold U. Bartels, Corona, Calif.

[73] Assignee: Bourns Medical Systems, Inc., Riverside, Calif.

[21] Appl. No.: 899,604

[22] Filed: Apr. 24, 1978

[51] Int. Cl.² ............................................. A61M 16/00
[52] U.S. Cl. .............................. 128/205.24; 137/528; 251/61.1
[58] Field of Search ............... 128/145.8, 145.5, 145.6, 128/145.7, 146.4, 146.5, 274, 188, 142.2; 251/61.1, 64, 333; 137/528

[56] References Cited

U.S. PATENT DOCUMENTS

| 3,394,732 | 7/1968 | Lisciani ............................ 251/333 X |
| 3,559,676 | 2/1971 | Haskins ........................... 251/61.1 X |
| 3,608,574 | 9/1971 | Beaussant ....................... 251/61.1 X |
| 3,861,642 | 1/1975 | Maddocks ........................... 251/61.1 |

FOREIGN PATENT DOCUMENTS

| 561896 | 5/1960 | Belgium ................................ 251/333 |
| 1227296 | 10/1966 | Fed. Rep. of Germany ........... 251/333 |

*Primary Examiner*—Henry J. Recla
*Attorney, Agent, or Firm*—William G. Becker

[57] ABSTRACT

A one-piece, integrally molded diaphragm for use in exhalation valves of respiratory apparatus to prevent the propagation of harmonic acoustic vibrations. High frequency oscillations are prevented from propagating by means of mechanical damping. The damper takes the form of a thin circular flutter sheet molded onto the face of the diaphragm and extending past the sealing area of a valve seat.

2 Claims, 3 Drawing Figures

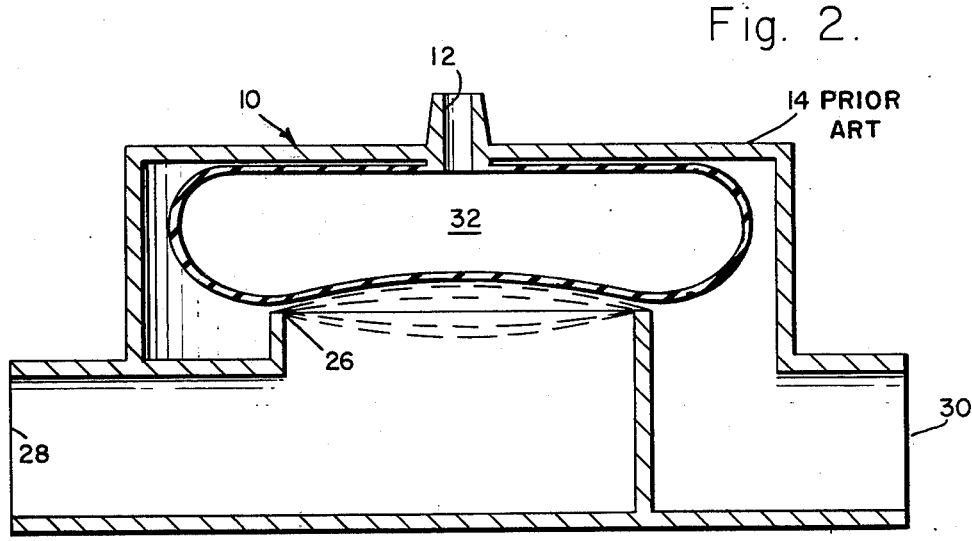
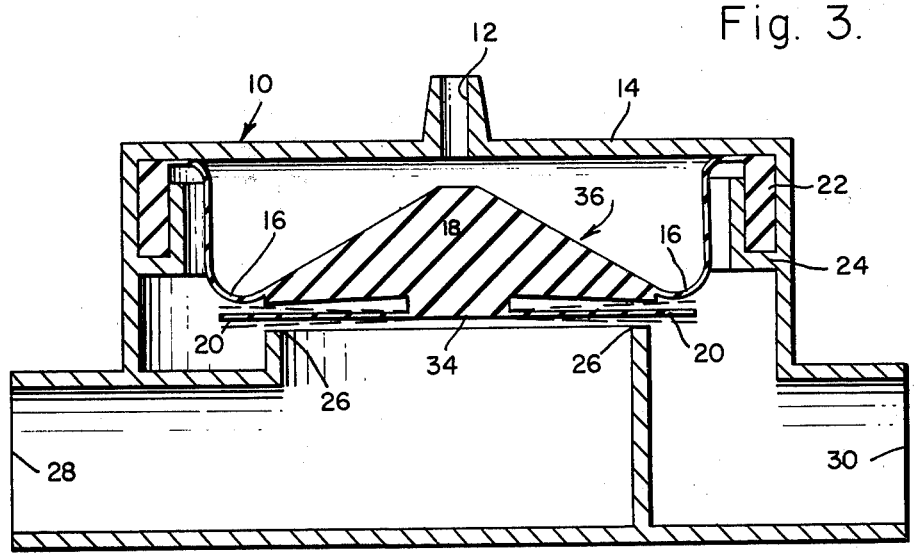

NOISE REDUCING EXHALATION VALVE AND DIAPHRAGM

BACKGROUND OF THE INVENTION

1. Field of the Invention

This invention relates generally to exhalation valves as used in patient respiratory systems and more particularly to noise reducing techniques in these respiratory systems.

2. Description of the Prior Art

The basic types of prior art exhalation valves and their diaphragms are well-known. These exhalation valves have been in use for many years and have met their special needs as presented by specific problems and have thus generally served narrow purposes. Some of these prior art devices have been described in the following listed patents, which were brought to the attention of the Applicant's attorney through a novelty search conducted in the United States Patent and Trademark Office:

| Number | Title | Inventor |
| --- | --- | --- |
| 2,705,608 | Non-Chattering Pilot Controlled Diaphragm Valve | G. M. Phillips |
| 3,559,676 | Antihunting Diaphragm Valves | L. D. Haskins |
| 3,584,621 | Respiratory Apparatus | F. M. Bird |
| 3,608,574 | Diaphragm-Valve Especially for a Respiratory-Gas Supply System | R. Beaussant |
| 3,822,819 | Fastener Driving Tool with Improved Valve | S. Wilson et al |
| 3,861,642 | Fluid Control Valve | G. E. Maddocks |

Many of these prior art devices have defects which render them inoperable with some respiratory systems. For example, some flow rate measurement systems are sensitive to acoustic disturbances and the measurements obtained under conditions including disturbances of this type are unreliable. Prior art exhalation valves used in respiratory therapy equipment generally have generated a wide spectrum of acoustical noise during the period when the patient exhales past a conventional partially pressurized exhalation valve diaphragm. Two or more frequencies of this spectrum may be amplified by components of the patient respiratory system to the point that they become objectionable in the form of annoying sound to the patient and disruption of the measuring processes of acoustically sensitive instruments, for example, vortex counting acoustic flowmeters.

Examples of major acoustic disturbances include an audible mid-range honk or moaning sound caused by sympathetic vibrations between associated tubing and the exhalation valve diaphragm, typically a very thin membrane, as it bows and stretches in response to pressure fluctuations upstream of the valve. Another disturbance manifests itself as a high frequency squeal that usually occurs at low flow rates and represents harmonic oscillations of an airspace in the valve as it is disturbed by a thin sheet of high velocity air issuing from the valve.

It would thus be a great advantage to the art to provide an exhalation valve for use in a patient respiratory system that neither generates nor propagates acoustic disturbances.

It would be a specific advantage to the art to provide such an exhalation valve that presents no annoying sounds to the patient.

It would be a further specific advantage to the art to eliminate disruptive acoustical disturbances to measuring instruments used in patient respiratory systems.

SUMMARY OF THE INVENTION

It is an object of the present invention to eliminate the mid-range honk and the high frequency squeal commonly encountered in patient respiratory systems in the operation of the exhalation valve.

It is a further object of the present invention to provide an exhalation valve for use in a patient respiratory system that neither generates nor propagates acoustic disturbances.

Yet another object of the present invention is the provision of an exhalation valve that presents no annoying sounds to the patient.

An additional specific object of the invention is the elimination of disruptive acoustical disturbances to measuring instruments used in patient respiratory systems.

In the accomplishment of these and other objects, a one-piece diaphragm is provided having a thick, stiff center section which prevents the "speaker effect" typical of thin diaphragms under conditions encountered in conventional exhalation valves. A thin flutter sheet, molded onto one face of the diaphragm, acts as a damper and thus prevents propagation of the high frequency oscillations.

BRIEF DESCRIPTION OF THE DRAWINGS

Further advantages and features of the present invention will be more fully apparent to those skilled in the art to which the invention pertains from the ensuing detailed description thereof, regarded in conjunction with the accompanying drawings wherein like reference characters refer to like parts throughout and in which:

FIG. 2 is a cross-sectional illustration of a prior art exhalation valve employing a conventional partially pressurized diaphragm.

FIG. 3 is a cross-sectional illustration of an exhalation valve employing a diaphragm as contemplated by the invention.

DETAILED DESCRIPTION

Figure 1:
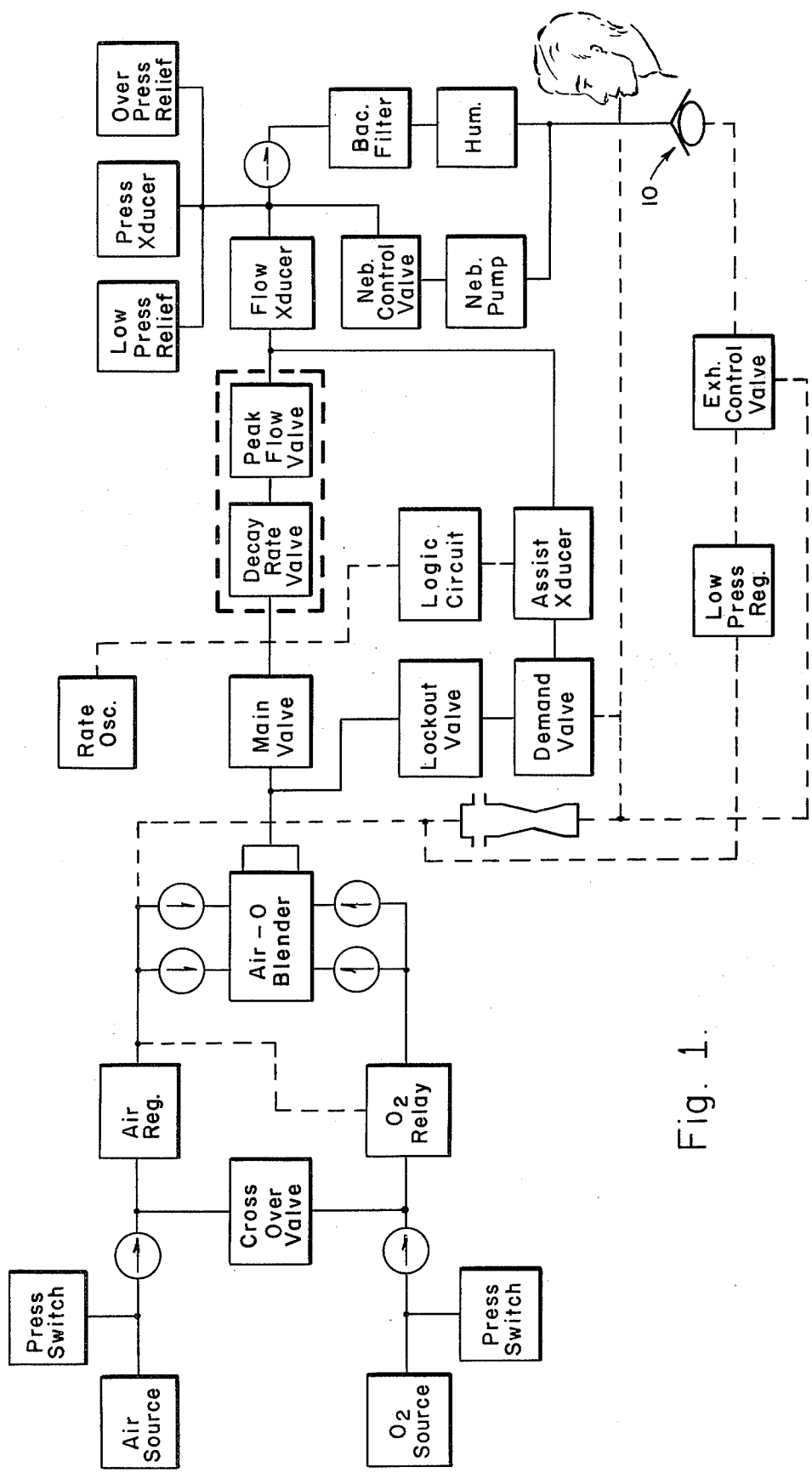
FIG. 1 is a block and schematic diagram of a conventional patient respiratory system.

Although specific embodiment of the invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are deemed to be within the spirit, scope and contemplation of the invention as further defined in the appended claims.

FIG. 1 may be used to explain the operation of a conventional medical respirator. Principle conduits which support the flow of breathing air to a patient are indicated by solid lines, while pilot lines serving principally to establish pressures at various locations within the respirator are indicated in dashed lines. Starting from the left-hand side of the figure, ambient air and oxygen are delivered from appropriate sources through check valves to opposite sides of a cross-over valve, which valve is opened by pressure switches. A regulator in the airline establishes a desired line pressure with a relay slaved to keep the oxygen line at the same pressure. The air and oxygen are delivered through check valves to the mixing valve or blender. The input gases are combined in desired proportions and supplied through conduits.

The main valve output is processed through a valve assembly, comprising a decay rate regulator or valve which controls the rate at which periodic flows of breathing gas decay from a peak value, and a peak flow valve which controls the maximum rate of flow to the patient. A flow transducer downstream from the valve assembly measures the gas volume delivered to the patient and closes the main valve when the desired volume has been delivered. Connected to the output of the flow transducer are low and over-pressure relief valves and a pressure transducer which activates appropriate alarms for adverse pressure conditions. The output of the flow transducer is delivered to the patient through a check valve, a bacteria filter, and a humidifier. Various medications may be added to the breathing gas flow by a nebulizer pump which is deactivated during patient exhalation by a control valve.

An alternate flow path from the mixing valve may be provided for an alternate mode, in which the respirator permits the patient to breathe on his own without delivering positive air flows. This path may include a demand valve which maintains the pressure in the system above a certain minimum level to prevent the patient's lungs from becoming unduly depressurized, a valve which locks out the demand valve, and an assist transducer which may operate to detect breath attempts and actuate the main valve in response thereto. An assist transducer may be connected to the output of the valve assembly so that breathing air flows in all modes are treated for bacteria, humidity, and medications. Other aspects of a typical respirator may include a venturi with a variable orifice for maintaining a positive pressure on the demand valve, thereby establishing a positive expiratory end pressure, an exhaust for expired air, and an expandable diaphragm which can block the exhaust during patient inhalation. The diaphragm is conventionally operated by a three-way exhalation control valve which connects it to the regulated pressure of the venturi during expiration, and to a low pressure regulator during inspiration. It is the operation of this diaphragm and its effect on the respiratory system that forms the basis for the present invention.

Referring now to FIG. 2, the operation of a conventional prior art exhalation valve employing a typical partially pressurized balloon-type exhalation valve diaphragm may be analyzed. The exhalation valve is denoted generally by the numeral 10 and the valve body by numeral 14. A patient exhalation flow port is identified by the number 28 and its associated patient exhalation overboard flow port by number 30. Flow through the valve 10 from port 28 to port 30 is controlled by the action of partially pressurized balloon-type exhalation valve diaphragm 32. This diaphragm may tend to be seated upon valve seat 26 under the action of an operating pressure applied through the operating pressure inlet port 12 situated in the valve body 14. Under critical conditions of flow through valve 10 coupled with a level of inflation of the partially pressurized balloon-type exhalation valve diaphragm 32 resulting in a small opening between diaphragm 32 and seat 26, the diaphragm may become alternately bowed and stretched at a frequency objectionable to a patient and to the operation of the system. Thus, the diaphragm in the vicinity of the valve seat may exhibit a tendency to oscillate between two positions as the face of the diaphragm approaches the valve seat. The velocity of the gas traveling across the valve seat 26 causes a drop in pressure, thus forcing the diaphragm 32 to seat. This sudden closing of valve diaphragm 32 is due, at least in part, to the velocity effect created by the high speed flow of gas across the valve seat 26 producing thereby a suction force tending to draw the diaphragm 32 against seat 26. As the face of the diaphragm 32 approaches valve seat 26, the diaphragm starts to hunt or oscillate between these two positions of completely open and completely closed. Upon this seating, however, the pressure of the gas entering the port 28 causes the diaphragm to unseat again in order to relieve that pressure. Resonant repetition of this process can cause honking and whistling in the system of the respirator. As noted in the foregoing, some of the frequencies of the wide spectrum of acoustical noise generated in this manner are usually amplified by components of the respirator system to the point that they become objectionable acoustically to the patient and functionally to sensitive equipment in the system.

Referring now to FIG. 3, the operation of a valve employing a diaphragm as contemplated by the invention may be explained. Again the exhalation valve is denoted generally by the numeral 10, while the valve body is identified by numeral 14. The operating pressure inlet port, as before, is called out by the numeral 12 and the patient exhalation flow port and patient exhalation overboard flow port respectively by the numerals 28 and 30. The valve seat is identified by the numeral 26.

Upon examining the structure of the diaphragm in greater detail, operation of the valve with respect to its noise elimination properties may be set forth. The diaphragm 36 is secured to the valve body by means of a securing flange 22 that fits into a retaining groove 24 in the valve body 14. Flexible extension 16 joins a frustum of a cone that forms the central portion 18 of the diaphragm to the securing flange 22. A boss 34 connects the cone-shaped central portion 18 to a thin circular flutter sheet 20. In operation, the thick, stiff center section of the cone-shaped central portion 18 prevents the low frequency "speaker effect" oscillations typical of thin diaphragms controlling varying flow in complex pneumatic systems. The thin circular flutter sheet 20 absorbs some of the energy in the high speed airstream and dissipates it as mechanical work by freely fluttering, thus no high frequency acoustical resonances are created. In experimental applications of the invention, the mass of the diaphragm 36 has been empirically tailored to the amount of energy to be dissipated and the thickness of the thin circular flutter sheet 20 designed with respect to the air velocity and critical noise frequency. In experimental tests with exhalation manifolds, all of which exhibited a variety of sounds at different positive end expiratory pressure levels within physiological flow ranges, utilization of the diaphragm structure of the invention successfully eliminated some acoustic frequencies and reduced the intensity of those remaining to below the threshold of sensitivity. It was thus observed that no audible noise was present to annoy and distract either patient or therapist. It was further importantly observed that no vibrations were thus induced so as to be erroneously recorded as expiratory flow by vortex-counting flowmeters.

Thus, there has been described a diaphragm to be used in an exhalation valve in a respiratory apparatus that will eliminate or greatly reduce acoustic disturbances occurring in such systems. Great improvements in reliability, flexibility, maintainability, ease of operation, and safety have been provided through the novel advantages of the invention.

It is pointed out that although the present invention has been shown and described with reference to particular embodiment, nevertheless various changes and modifications obvious to one skilled in the art to which the invention pertains are deemed to lie within the purview of the invention.

What is claimed and desired to be secured by Letters Patent of the United States is:

1. A noise reducing exhalation valve for use with medical respiratory systems comprising:
   valve body means;
   patient exhalation flow port means in said valve body means for accepting expiratory fluid flow from a patient using said medical respiratory system;
   valving means in said valve body means in fluidic communication with said patient exhalation flow port means to control fluid flow by permitting and restricting said expiratory fluid flow therethrough;
   operating control pressure chamber means in said valve body;
   operating pressure inlet port means communicating with said operating control pressure chamber means for admitting fluid operating pressures to said valve body means for controlling said valving means;
   said valving means including a valve seat in said patient exhalation flow port means and an integrally molded diaphragm means in said valve body means responsive to said fluid operating pressures supplied by way of said operating pressure inlet port means and operable with said valve seat to open and close said valving means, said diaphragm means and said body means defining said operating control pressure chamber means, said integrally molded diaphragm means comprising:
   a cone-shaped central portion;
   a cylindrical boss, one base of which is integrally molded onto the flat surface of said cone-shaped central portion;
   a thin circular sheet integrally molded to the other base of said cylindrical boss;
   a flexible extension integrally molded to the periphery of said cone-shaped central portion;
   a securing flange integrally molded to the periphery of said flexible extension;
   retaining groove means in said valve body means for receiving and securing said securing flange; and
   patient exhalation overboard flow port means in fluid communication with said patient exhalation flow port means by way of said valving means for exhausting said expiratory fluid flow exhaled by a patient using said medical respiratory system.

2. In a medical respiratory system having a valve body which includes a patient exhalation flow port for accepting expiratory fluid flow from a patient using the medical respiratory system and valving means fluidically communicating with said patient exhalation flow port to control fluid flow by permitting and restricting said expiratory fluid flow therethrough, said valving means including a valve seat in said patient exhalation flow port and a valve member in said valve body operatively associated with said valve seat, operating control pressure chamber means in said valve body, and further having an operating pressure inlet port communicating with said operating control pressure chamber means for admitting fluid operating pressures into said valve body for controlling said valve member, the improvement comprising:
   said valve member including an integrally molded diaphragm responsive to said fluid operating pressures supplied by way of said operating pressure inlet port and operable with said valve seat to open and close said exhalation port, said integrally molded diaphragm means comprising:
   a cone-shaped central portion;
   a cylindrical boss, one base of which is integrally molded onto the flat surface of said cone-shaped central portion;
   a thin circular sheet integrally molded to the periphery of the other base of said cylindrical boss;
   a flexible extension integrally molded to the periphery of said cone-shaped central portion;
   a securing flange integrally molded to said flexible extension;
   said diaphragm means and said valve body defining said operating control pressure chamber means;
   retaining groove means in said valve body means for receiving and securing said securing flange; and
   patient exhalation overboard flow port means in fluid communication with said patient exhalation flow port by way of said valving means for exhausting said expiratory fluid flow exhaled by a patient using said medical respiratory system.

* * * * *

UNITED STATES PATENT OFFICE
CERTIFICATE OF CORRECTION

Patent No. 4,190,045          Dated February 26, 1980

Inventor(s) Harold U. Bartels

It is certified that error appears in the above-identified patent and that said Letters Patent are hereby corrected as shown below:

Column 2, line 59:   "Principle" should read -- Principal --

Column 6, lines 34 & 35:   remove "the periphery of"

Column 6, line 38:   add after "to", the words -- the periphery of --

Signed and Sealed this

Nineteenth Day of August 1980

[SEAL]

Attest:

SIDNEY A. DIAMOND

Attesting Officer      Commissioner of Patents and Trademarks